(12) United States Patent
Pinchuk

(10) Patent No.: US 6,197,240 B1
(45) Date of Patent: Mar. 6, 2001

(54) METHOD OF DEVICE HAVING BIOSTABLE ELASTOMERIC POLYMERS HAVING QUATERNARY CARBONS

(75) Inventor: Leonard Pinchuk, Miami, FL (US)

(73) Assignee: Corvita Corporation

(*) Notice: Subject to any disclaimer, the term of this patent is extended or adjusted under 35 U.S.C. 154(b) by 0 days.

(21) Appl. No.: 09/309,007

(22) Filed: May 10, 1999

Related U.S. Application Data

(62) Division of application No. 08/951,016, filed on Oct. 15, 1997, now Pat. No. 6,102,939, which is a division of application No. 08/681,809, filed on Jul. 29, 1996, now Pat. No. 5,741,331.

(51) Int. Cl.[7] .................................................... B29C 41/08
(52) U.S. Cl. .................... 264/309; 264/310; 264/331.15; 264/331.17; 264/331.18; 427/2.1; 427/2.25
(58) Field of Search .................................... 264/309, 310, 264/330, 331.11, 331.15, 331.17, 331.18; 427/2.1, 2.24, 2.25

(56) References Cited

U.S. PATENT DOCUMENTS

| | | |
|---|---|---|
| Re. 34,640 | 6/1994 | Kennedy et al. . |
| 4,226,230 | 10/1980 | Potts . |
| 4,276,394 | 6/1981 | Kennedy et al. . |
| 4,316,973 | 2/1982 | Kennedy . |
| 4,342,849 | 8/1982 | Kennedy . |
| 4,851,009 * | 7/1989 | Pinchuk ................................ 623/66 |
| 4,855,335 | 8/1989 | Neperud . |
| 4,873,308 | 10/1989 | Coury et al. . |
| 4,882,148 | 11/1989 | Pinchuk . |
| 4,910,321 | 3/1990 | Kennedy et al. . |
| 4,929,683 | 5/1990 | Kennedy et al. . |
| 4,941,870 | 7/1990 | Okada et al. . |
| 4,946,899 | 8/1990 | Kennedy et al. . |
| 5,066,730 | 11/1991 | Kennedy et al. . |
| 5,122,572 | 6/1992 | Kennedy et al. . |
| 5,133,742 | 7/1992 | Pinchuk . |
| 5,229,045 * | 7/1993 | Soldani ................................ 264/310 |
| 5,229,431 * | 7/1993 | Pinchuk ................................ 521/159 |
| 5,242,983 | 9/1993 | Kennedy et al. . |
| 5,254,662 * | 10/1993 | Szycher et al. ....................... 528/67 |
| 5,266,325 * | 11/1993 | Kuzma et al. ....................... 264/310 |
| 5,630,844 | 5/1997 | Dogan et al. . |
| 5,741,331 | 4/1998 | Pinchuk . |

FOREIGN PATENT DOCUMENTS

| | | |
|---|---|---|
| 0 461 375 A1 | 12/1991 | (DE) . |
| 0797963 A2 | 10/1997 | (EP) . |
| 94861 | 6/1983 | (JP) . |

* cited by examiner

Primary Examiner—Jan H. Silbaugh
Assistant Examiner—Kenneth M. Jones
(74) Attorney, Agent, or Firm—Ratner & Prestia

(57) ABSTRACT

An article of manufacture and method of making and implanting the article made of a polyolefin star or linear copolymer are disclosed in which the polyolefin copolymer is biostable and crack-resistant when implanted in vivo. The polyolefin copolymer is the reaction product of a rubbery component which when homopolymerized produces a polymer having a low level of hardness, and a hardening component which when homopolymerized produces a polymer having a high level of hardness. The polyolefin copolymer is elastomeric, has a hardness intermediate the low and high levels of hardness, and has a backbone in which the majority of polymer linkages along the copolymer chain are alternating quaternary and secondary carbon atoms.

20 Claims, 2 Drawing Sheets

METHOD OF DEVICE HAVING BIOSTABLE ELASTOMERIC POLYMERS HAVING QUATERNARY CARBONS

RELATED APPLICATIONS

This application is a division of application Ser. No. 08/951,016, filed Oct. 15, 1997, now U.S. Pat. No. 6,102,939, which application is a division of application Ser. No. 08/681,809, filed Jul. 29, 1996, now U.S. Pat. No. 5,741,331.

BACKGROUND AND DESCRIPTION OF THE INVENTION

The present invention generally relates to implantable prostheses and the like which are formed in a manner to substantially prevent cracking, crazing or degradation thereof when they are implanted or otherwise subjected to degradation conditions. A medical prosthesis or the like according to this invention includes a polyolefinic elastomeric triblock star or linear copolymer where the backbone comprises alternating units of quaternary and secondary carbons which will not crack or degrade when subjected to implantation for substantial time periods during which other types of polymers would crack or degrade.

Several biocompatible materials which are quite suitable for use in making implantable medical devices that may be broadly characterized as implantable prostheses exhibit properties that are sought after in such devices, including one or more of exceptional biocompatibility, extrudability, moldability, good fiber forming properties, tensile strength, elasticity, durability and the like. However, many of these otherwise highly desirable materials exhibit a serious deficiency when implanted within the human body or otherwise subjected to harsh environments, such deficiency typically being manifested by the development of cracks or fissures. For example, surface fissuring or cracking occurs after exposure of on the order of one month or more, or shorter time periods depending upon the materials and the implant conditions, to body fluids and cells such as are encountered during in vivo implantation and use.

It is desirable that long-term implantable elastomers, such as those used for vascular grafts, endoluminal grafts, intraocular lenses, finger joints, indwelling catheters, pacemaker lead insulators, breast implants, heart valves, knee and hip joints, vertebral disks, meniscuses, tooth liners, plastic surgery implants, tissue expanders, drug release membranes, subcutaneous ports, injection septums, etc., be stable for the duration of the life span of the recipient.

Polymers that are not stable in the physiological environment tend to crack and degrade with time. There are many implant applications where this type of behaviour cannot be tolerated. For example, pacemaker lead insulators can form current leaks thereby causing the wires to short out and the pacemaker to be rendered non-functional. It is therefore desirable to have a material for long-term use that is both elastomeric and does not degrade in the body.

Several theories have been promulgated in attempting to define the cause of this undesirable cracking phenomenon. Proposed mechanisms include oxidative degradation, hydrolytic instability, enzymatic destruction, thermal and mechanical failure, immunochemical mechanisms, inhibition of lipids and combinations of the above. Prior attempts to control surface fissuring or cracking upon implantation or the like have included incorporating antioxidants within a biocompatible polymer and subjecting the biocompatible polymer to various different annealing conditions, typically including attempting to remove stresses within the polymer by application of various heating and cooling conditions. Attempts such as these have been largely unsuccessful.

Other treatment approaches have been utilized, or attempted, to increase the structural stability of especially desirable materials. Included in the biocompatible materials which are desirable from many points of view, but which exhibit a marked tendency to crack or degrade over time, are the polyurethane materials and other biocompatible polymers that are of an elastomeric nature. It is particularly advantageous to use these types of materials for making products in which compliance and/or flexibility, high tensile strength and excellent fatigue life are desirable features. One basic approach which has been taken in the past in order to render these materials more suitable for implantation and other applications where material degradation can develop, has been to treat the material with so-called crack preventatives. Exemplary approaches in this regard are found in my U.S. Pat. Nos. 4,769,030, 4,851,009 and 4,882,148, the subject matter of which is incorporated by reference herein. Sulfonation of polyurethanes to prevent cracking is also described in my U.S. Pat. No. 4,882,148, the subject matter which is also incorporated by reference herein. Such treatments, of course, require additional procedures, and post processing of the implantable article, thereby complicating manufacturing procedures, increasing expense and complexity and, if not coated or treating properly and entirely, are subject to delamination and failure. It would be advantageous if the material out of which the product is made would itself have the desired properties. It is also advantageous for the material to be compatible with other materials that are commonly used in the medical fields, such as with adhesives, surface coatings and the like.

An especially difficult problem is experienced when attempting to form prostheses with procedures including the extrusion or spinning of polymeric fibers, such as are involved in winding fiber-forming polymers into porous vascular grafts or similar products, for example as described in U.S. Pat. No. 4,475,972 (Wong), the subject matter of which is also incorporated by reference herein. Such vascular grafts or the like include a plurality of strands that are of a somewhat fine diameter size such that, when cracking develops after implantation, this cracking often manifests itself in the form of complete severance of various strands of the device. Such strand severance cannot be tolerated to any substantial degree and still provide a device that can be successfully implanted or installed on a generally permanent basis whereby the device remains viable for a number of years.

There is accordingly a need for a material which will not experience surface fissuring or cracking under implanted or in vivo conditions and which is otherwise desirable and advantageous as a material for medical devices or prostheses that must successfully delay, if not eliminate, the cracking phenomenon even after implantation for months and years, in many cases a substantial number of years. Exemplary medical devices or prostheses for which such a non-cracking material would be especially advantageous include those which have been previously discussed.

The only elastomers that are currently implanted are polyurethanes, as previously discussed, and silicone rubbers.

The silicone rubbers, most notably polydimethylsiloxane, are probably the most stable elastomers used in the body. However, there have been many reported instances where they do not perform well. For example, silicone rubber poppet valves for coronary valve replacement tend to swell and crack with time, heart valve leaflets tend to calcify, silicone gel-filled breast implant shells tend to plasticize with silicone oils and in many instances, rupture with time. The mechanism of biodegradation of silicones in the body is believed to involve oxidative pathways.

Three families of polyurethanes have been used in long-term implant applications; i.e. the polyester urethanes which have been used as foamed coatings on some breast implants, the polyether urethanes which have been used as insulators on pacemaker leads, and the polycarbonate urethanes for use in vascular grafts. Polyether and polyester urethanes have repeatedly been shown to degrade with time in the body. L. Pinchuk, *A Review of The Biostability and Carcinogenity of Polyurethanes in Medicine and the New Generation of "Biostable" Polyurethanes*, J. Biomaterial Science, Polymer Ed., Vol. 6, No. 3, pp 225–267 (1994).

The more recent family of biostable elastomeric polyurethanes which contain polycarbonate groups, rather than other or ester groups, are described in my U.S. Pat. Nos. 5,133,742 and 5,229,431, the subject matter of which is incorporated by reference herein. A similar polycarbonate urethane, but of a lower modulus of elasticity, is disclosed in U.S. Pat. No. 5,254,662 (Szycher et al). All of these polymers have demonstrated much improved biostability as compared to the polyether and polyester urethanes. However, as also described in my last mentioned review, some cracking and fiber breakage are observed on microfibers comprising a polycarbonate urethane vascular graft with time.

Still another biostable polyurethane is described in U.S. Pat. No. 4,873,308 (Coury et al). It is formed of all aliphatic soft segments of predominantly consecutive secondary carbon atoms. Two potential weaknesses of this polymer are that the secondary carbon atoms can oxidize with time, and the urethane linkages present on the backbone can hydrolyze with time. In addition, as reported in my aforementioned review, the polymer weakens with exposure to moisture and has a modulus with a yield point.

Again referring to my aforementioned review, a number of investigators have demonstrated that biodegradation of materials is usually a result of oxidation. Cells, especially leukocytes, secrete superoxide and hydrogen ions which subject the material to high concentrations of oxidants (free radicals) and strong acids. It is therefore a principal purpose of this invention to formulate long-term implantable materials with molecules that are not readily susceptible to oxidation and to attack by acid.

Two non-elastomeric polymers that have performed well in the body include polytetrafluoroethylene (Teflon) and polymethylmethacrylate with few, if any, reports of biodegradation. Other polymers in addition to those already discussed that have also enjoyed some measure of success in the body, but do demonstrate some degree of biodegradation with time, include polypropylene, polyethylene and to some degree polyester terephthalate (PET).

Examination of the chemistry of those polymers reveal that, except for polytetrafluoroethylene, which is inert due to the replacement of all hydrogens with fluorine, the most inert polymers are those with the most "quaternary" carbons, as defined below. The principal problem with all of these polymers is that they are non-elastomeric and, therefore, cannot be used in certain applications in the body, such as vascular or endoluminal grafts where elasticity is desired.

Polymethylmethacrylate has repeating units of:

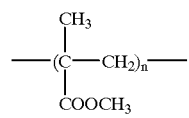

Polypropylene has repeating units of:

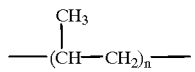

Polyethylene has repeating units of:

The number of repeating units is usually sufficiently large so that the molecular weight of the polymer is in excess of 60,000 Daltons. It will be seen that polyethylene is comprised only of "secondary" carbons, i.e. each carbon atom on its backbone is bonded to two other carbon atoms. Polypropylene has alternating "secondary" and "tertiary" carbons. A "tertiary carbon" is a carbon that is bonded to three other carbon atoms. A "quaternary" carbon is a carbon that is bonded to four other carbon atoms. The polymethylmethacrylate has a backbone of alternating "quaternary" carbons and "secondary" carbons.

Further examination of polyethylene will reveal that, in the presence of free radicals and other oxidizing agents, the polyethylene molecule and its secondary carbons can undergo abstraction of hydrogens and the formulation of free radicals and double bonds, e.g.

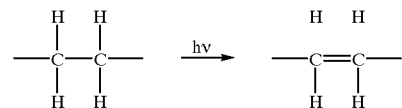

Double bonds can also lead to intermolecular or intramolecular crosslinking. Once the double bond, unsaturation or crosslinking forms in the polymer, the polymer can become embrittled leading to cracking or degradation. For this reason polyethylene is hardly used anymore for pacemaker lead insulators, because it embrittles and then cracks and flakes with flexion in the body.

Similarly, but not as frequently, polypropylene can oxidize to the formation of a double bond between the tertiary carbon and the secondary carbon, i.e.

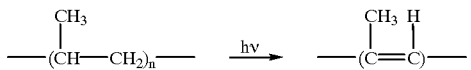

Polypropylene, when loaded with antioxidants, is successfully used as a suture in the body, but does show some degradation with time as a haptic on intraocular lenses.

On the other hand, polymethylmethacrylate, has quaternary and secondary carbons along its backbone. Therefore, it is not readily susceptible to oxidation. Formation of a double bond along the backbone of the polymer would require the cleavage of carbon to carbon bonds, i.e.

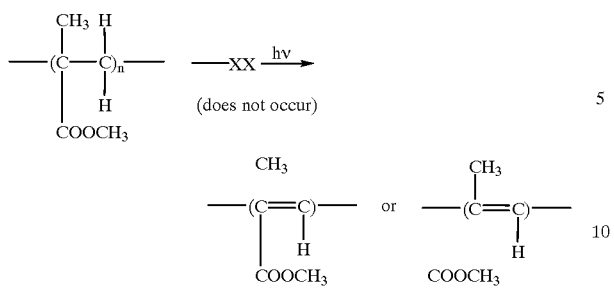

(does not occur)

rather than carbon to hydrogen bonds as in the secondary and tertiary carbons. Extremely high energies are required to break carbon to carbon bonds. It is for this reason that polymers with alternating quaternary and secondary carbon bonds are very stable in the body.

The problem with the polymethylmethacrylate, polypropylene and polyethylene polymers is that they are not elastomers. They are rigid engineering plastics. Therefore, they cannot satisfy a need in the medical industry for a flexible polymer with excellent oxidation resistance, such as one that has alternating units of quaternary and secondary carbons.

The present invention achieves these objectives with a polymer which is a polyolefinic elastomer of a triblock star or linear copolymer backbone having alternating units of quaternary and secondary carbons. The polymer should have a resultant hardness which is between about Shore 20A–75D, and preferably between about Shore 40A and Shore 90A.

Accordingly, a general object of the present invention is to provide improved crack-resistant devices and products.

Another object of the present invention is to provide a polymeric material and products made therefrom which are particularly resistant to cracking and degradation, even under in vivo conditions.

Another object of the present invention is to provide an improved polyolefin material which can be spun through a spinnerette or extruded through and/or into suitable molding devices into products which exhibit superior crack-resistant properties, and/or which can be injection or compression molded, solvent castable, or solvent sprayable into such products.

Another object of the invention is to provide improved implantable devices and/or prostheses which exhibit an exceptional ability to prevent the formation of cracks and strand severance upon implantation for substantial time periods, such as those needed for generally permanent implantation procedures.

Another object of the present invention is to provide an improved vascular graft and the like that is made from spun fibers of polymer and that exhibits exceptional stability with respect to crack formation and strand severance development under in vivo conditions.

These and other objects, features and advantages of the present invention will be clearly understood through a consideration of the following detailed description.

BRIEF DESCRIPTION OF THE DRAWINGS

In the course of this description, reference will be made to the attached drawings, in which.

DESCRIPTION OF THE PREFERRED EMBODIMENTS

Figure 1:
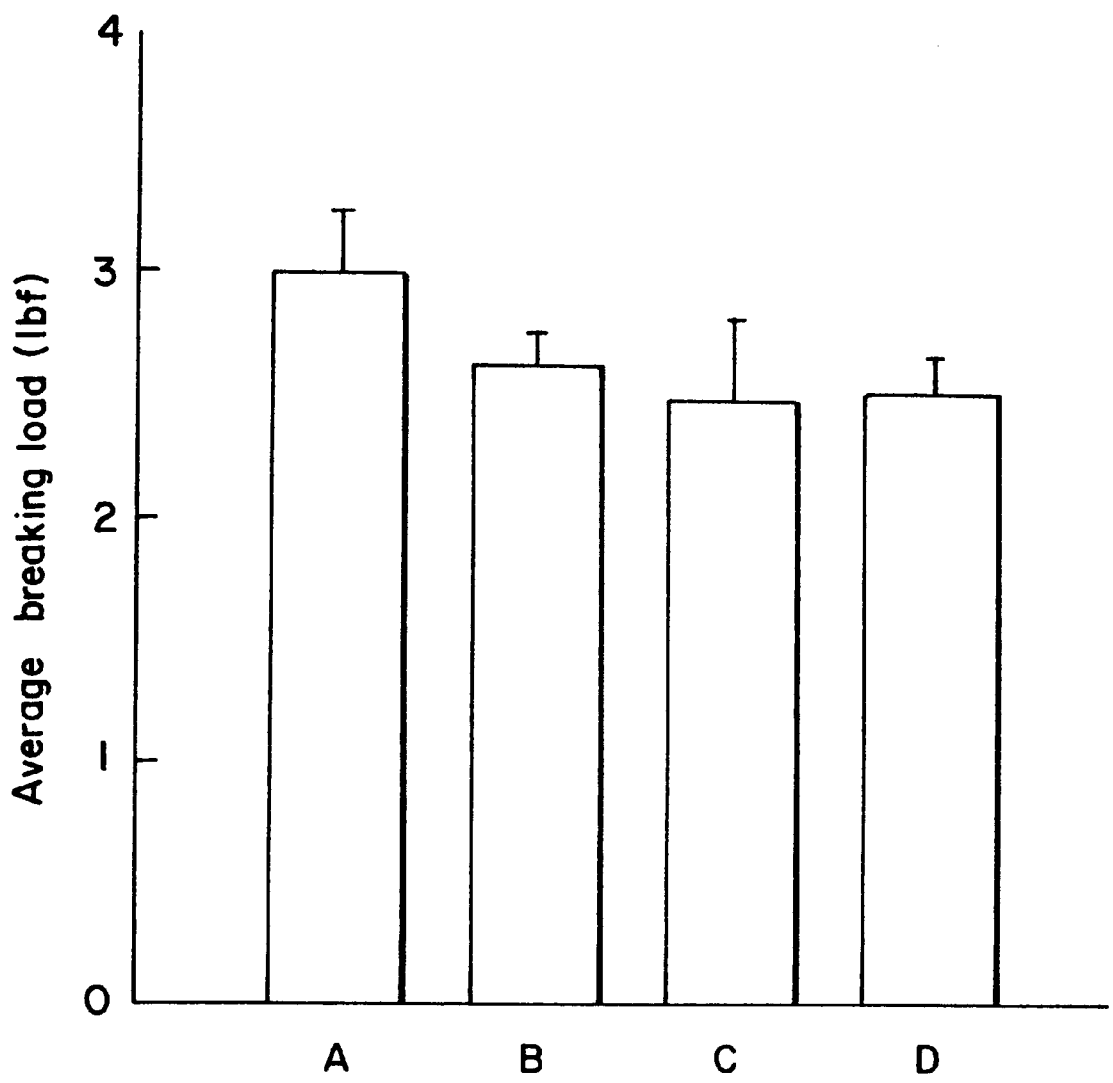
FIG. 1 is a graph which shows the performance of monofilament samples of the triblock copolymers of the invention in breaking load tests and before implant and following in vivo explant.

In the preferred embodiments of the present invention, a polymer is provided which is a polyolefinic elastomer having a backbone which comprises a triblock linear or star copolymer having alternating units of quaternary and secondary carbons. The term "secondary" carbons, as previously defined, means carbon atoms which are bonded to two other carbon atoms. The term "tertiary" carbons, as previously defined, means carbon atoms that are bonded to three other carbon atoms. The term "quaternary" carbons, as previously defined, means carbon atoms which are bonded to four other carbon atoms.

The polyolefinic elastomer copolymer of the present invention contains at least two components I and II.

Component I is a rubbery or soft segment component which is based upon a repeating unit of a quaternary carbon and a secondary carbon, having the following general formulation:

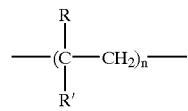

where R and R' are aliphatic moieties, such as methyl, ethyl, propyl, butyl, pentyl, hexyl or cyclic aliphatic groups. The preferred rubbery component I is polyisobutylene (PIB) with the following structure:

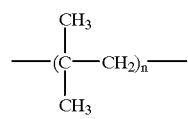

Pure polymers of PIB are commercially available. One of their principal uses is as the gum stock in chewing gum. Crosslinked or vulcanized PIB is used as inner tubes in tires, and simple low molecular weight PIB chains are used in high temperature lubricants.

High molecular weight PIB is a soft material with a Shore hardness of approximately 10A to 30A. When combined with other block copolymers, it can be made at hardnesses ranging up to the hardness of the copolymer. For example, if it is copolymerized with polystyrene, and if the polystyrene has a Shore hardness of 100D, depending upon the relative amounts of styrene and isobutylene, the resultant polymer can have a range of hardnesses from as soft as Shore 10A to as hard as Shore 100D.

Component II of the block copolymer is a hardening component. It may include any one of a number of monomers or polymers as long as the majority of polymer linkages along the copolymer chain are comprised of alternating quaternary and secondary carbons, and the hardening component II, when combined with the rubbery or soft component I, is capable of altering or adjusting the hardness of the rubbery or soft component so that the ultimate polyolefin copolymer has the desired elastomeric and hardness qualities. Typical hardening component comonomers of copolymers used as copolymers or block copolymers, or more specifically triblock copolymers, with polyisobutylene (PIB) in the present invention are styrene, α-methylstyrene, methylmethacrylate, ethylmethacrylate, hydroxyethyl methacrylate and the like.

Although PIB can be polymerized anionically, it is probably best polymerized under controlled means using carbocationic polymerization techniques such as those described in U.S. Pat. Nos. 4,276,394, 4,316,973, 4,342,849, 4,910,321, 4,929,683, 4,946,899, 5,066,730, 5,122,572 and/or Re. 34,640, the subject matter of which is incorporated by reference herein. These materials may involve telechelic starting molecules, with block derived therefrom. Although the description to follow of the invention is set forth in terms of linear copolymers which are formed from ditelechelic starting materials, star copolymers are formed simply by using tri- rather than ditelechelic starting molecules and as disclosed in the above identified patents.

The polyolefinic copolymer elastomer of the present invention has the general formulation:

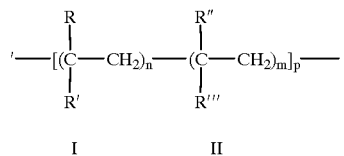

and more preferably:

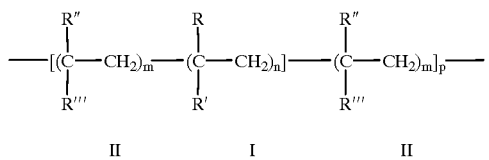

where R and R' are non-cyclic or cyclic aliphatic moieties, such as methyl, ethyl, propyl, butyl, pentyl, hexyl, heptyl and octyl groups with pendant aliphatic groups such as methyl, ethyl or propyl groups, preferably methyl groups, R" is a hydrogen, hydroxyl, methyl or ethyl group, and R''' is an aromatic (phenyl, benzyl or substituted benzyl) group, $COOCH_3$, methoxy, ethoxy, aliphatic, cycloaliphatic, substituted aliphatic or other group, and such that homopolymers of

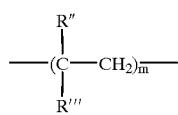

are high hardness materials.

The rubbery component and hardening component I and II respectively are shown in the above copolymer formulations. The amount of hardening component II in the copolymer is preferably between about 20 wt % to 80 wt %, and more preferably between about 30 wt % to about 50 wt %.

Repeating units n and m should range from about 250 to about 5000, and of p should range from about 1–10, with about 1 being typical. The combined molecular weight should be in excess of 60,000 Daltons, and preferably between about 90,000 to about 300,000 Daltons. Triblocks of PIB with polystyrene or polymethylstyrene are preferred polyolefin elastomeric copolymers of the invention and these may be made as described in U.S. Pat. No. 4,946,899, the subject matter of which is incorporated herein by reference.

The copolymers of the present invention are preferably copolymerized in solvents. The solvents may be non-polar solvents, polar solvents or mixtures thereof. Suitable non-polar solvents include hexane, cyclohexane, heptane, methylene chloride, toluene, Freon®, low molecular weight silicones and the like. Suitable polar solvents include methanol, ethanol, propanol, tetrahydrofuran and the like. The solvent may also comprise a binary blend of the previously mentioned non-polar and polar solvents. For example, where the triblock copolymer is of isobutylene and styrene, the solvent is preferably a binary solvent of heptane in which isobutylene is soluble and methanol in which styrene is soluble.

Other components such as antioxidants, extrusion agents and the like can be included, although typically there would be a tendency and preference to exclude such additional components when a medical-grade polymer is being prepared.

While no treatment of the polyolefin copolymer products according to this invention is required, suitable treatments can be conducted if desired. For example, they may be subjected to treatment with a crack preventative composition that includes an elastomeric silicone such as poly(dimethyl siloxane), as described in detail in my U.S. Pat. No. 4,851,009.

EXAMPLE 1

A potent in vitro screen for biostability is boiling the sample in concentrated (65%) nitric acid. Nitric acid is both a strong oxidant and a strong acid.

Samples that have enjoyed some success in the body, such as the polyether urethanes, polyester urethanes, polycarbonate urethanes, Dacron (polyester terephthalate), Nylon 11, silicon rubber, natural rubber, PEEKEK (poly(ether-ether-ketone-ether-ketone)), polyethylene, polypropylene and polymethylmethacrylate were subjected to 65% boiling nitric acid for up to 30 minutes. Also included was a sample of a carbocationically produced polyisobutylene and a copolymer according to the present invention which was a triblock polymer of styrene-PIB-styrene of 38 wt % styrene. The results are presented in Table 1.

TABLE 1

| Sample | Time to dissolution | Results | Tensile Strength Remaining |
|---|---|---|---|
| Polyether Urethane | <3 seconds | destroyed | 0 |
| Polyester Urethane | <5 seconds | destroyed | 0 |
| Polycarbonate Urethane | <10 seconds | destroyed | 0 |
| Dacron Fiber | <10 seconds | destroyed | 0 |
| Nylon 11 | <30 seconds | destroyed | 0 |
| Natural Rubber | <50 seconds | destroyed | 0 |
| crosslinked polycarbonate urethane | no dissolution | very Brittle | ~0 |
| PEEKEK Fiber | no dissolution | very brittle | ~0 |
| Silicone | no dissolution | very | ~10% |

TABLE 1-continued

| Sample | Time to dissolution | Results | Tensile Strength Remaining |
|---|---|---|---|
| rubber | | brittle | |
| Polyethylene (low density) | no dissolution | very brittle | ~50% |
| PIB (homopolymer) | no dissolution | plastic deformation* | ~60% |
| polypropylene | no dissolution | no change | ~100% |
| Polymethy-methacrylate | no dissolution | no change | ~100% |
| Polystyrene | no dissolution | no change | ~100% |
| Teflon | no dissolution | no change | ~100% |
| Sty-PIB-sty (38 wt % Styrene) | no dissolution | no change | ~100% |

*Melting point too low in sample tested.

The polymers degraded in the same order as is observed in vivo; i.e. the polyether urethanes were destroyed first, followed by the polyester urethanes, followed by the polycarbonate urethanes, then Dacron, Nylon 11, then silicon rubber, etc. with no measurable degradation of polytetrafluoroethylene (Teflon) or polymethylmethacrylate. This validates this in vitro boiling nitric acid test of biostability.

The PIB homopolymer was a mixture of different molecular weight polyisobutylenes and demonstrated plastic deformation due to partial melting of the polymer.

The triblock polymer of styrene-PIB-styrene of the invention did not show any signs of degradation over the entire duration of the test and remained pliable and elastomeric. The fast that this triblock polymer did not degrade in concentrated boiling nitric acid is strong evidence that it is stable in the body for long durations.

EXAMPLE 2

A linear triblock copolymer resin of styrene-PIB-styrene of 34 wt % styrene according to the present invention was prepared. This copolymer resin was melt extruded from a cylinder through a heated orifice with a piston under pressure to form a continuous monofilament of the copolymer 1 mm in diameter. The monofilament was cut into two inch long samples. Some of the samples were sterilized in ethylene oxide, and some of the sterilized samples were implanted subcutaneously in the back of dogs for two and four weeks, respectively. Following explant of the samples which had been implanted, three of each of the following samples were tested under load to determine their breaking strength on an Instron Tensile Testing Machine, Model No. 1011:

A—control, unsterilized, and not implanted.
B—control, sterilized but not implanted.
C—sterilized, implanted and explanted after 2 weeks.
D—sterilized, implanted and explanted after 4 weeks.

The results of the load tests are shown in FIG. 1. The "T" extensions shown on top of each of the bars in the FIG. 1 graph shows the high load value at which the filament being load tested broke. The top of each bar shows the average mean load value at breaking. Although not shown in FIG. 1, if the "T" extension of each bar was 180° inverted to extend beneath the top of its bar, the minimum load value at which the filament being load tested broke would be depicted. Thus, by way of example the average mean load at which the control sample A broke was about 3 pounds force, the high load value was about 3.2 pounds force, and the minimum load value was about 2.8 pounds force.

The difference in pounds force between samples A–D observed in the load tests and shown in FIG. 1 are not significant. According, FIG. 1 further shows that the triblock polymers of the invention are highly resistant against degradation under in vivo conditions.

EXAMPLE 3

The linear triblock polymer of the invention and as described in Example 2 was formed into a porous non-woven membrane. To do so, the triblock polymer was dissolved in the amount of 6% solids in tetrahydrofuran. This solution was sprayed with an air brush onto a rotating mandrel. The environment was controlled during spraying so that the tetrahydrofuran evaporated between the sprayer and the mandrel and so that a porous mat was formed on the rotating mandrel. These samples were then fully dried in air and removed from the mandrel.

Figure 2:
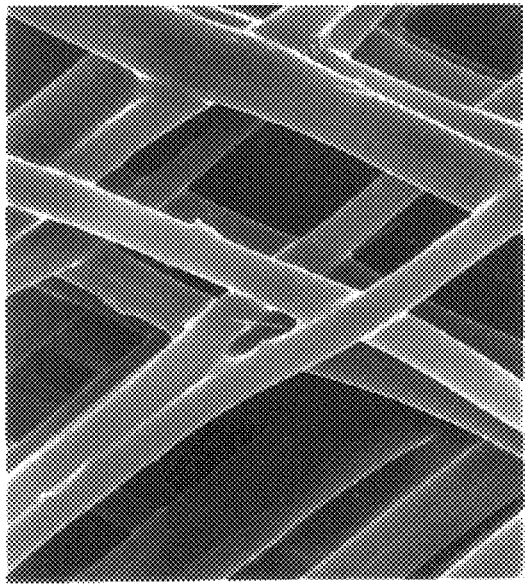
FIGS. 2 and 3 are photomicrographs of sections of polyether urethane material samples which respectively have not and have been in vivo implanted and of the kind which has previously been employed in in vivo implant use.

A known polyether urethane was also formed into a non-woven membrane. The polyether urethane was of the kind which is regularly employed as implantable pacemaker leads and was Pellethane 2363-80A from Dow Chemical, Midland, Mich. Pellets of the polyether urethane were dissolved in the amount of 45% solids in dimethyl acetamide while agitating and heating. This solution was pumped through a spinneret with 30 orifices on a shuttle that reciprocated back and forth along a rotating mandrel so that the continuous fibers which issued from the spinneret orifices were wound on the mandrel. As with the polymer of the invention, the dimethyl acetamide environment was controlled during spraying so that the dimethyl acetamide evaporated between the spinneret and the mandrel. Each pass of the reciprocating spinneret deposited fibers at an angle on the preceding fibers to form a non-woven mat, as shown in FIG. 2, and in which the fibers were about 10–20 microns in diameter. These fibers were about 2–5 times larger in diameter than the diameter of the fibers or strands of the triblock polymer previously described in this example.

Both the triblock polymer and polyether urethane samples which had been so prepared were then cut into approximately rectangular samples which were about 1 cm by 2 cm and about 0.2 mm thick. Some of each of these respective samples were then implanted subcutaneously in the back of dogs. After one month in the case of the polyether urethane implants and three months in the case of the triblock polymer, these samples were removed from the dogs. These explants were soaked upon their respective removal in a sodium hydroxide (10%) and sodium hypochlorite (7%) solution for 24 hours to remove ingrown tissue. They were then sputtered with gold and examined under a scanning electron microscope.

Figure 3:
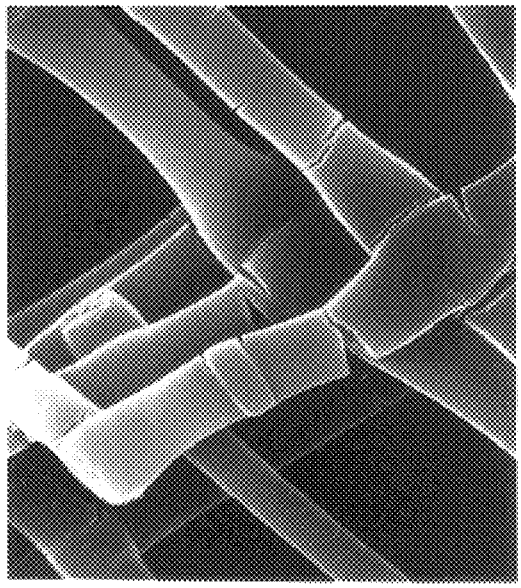

FIGS. 2 and 3 are reproductions of photomicrographs of the previously known polyether urethane samples at 200× under the electron microscope. FIG. 2 shows on of the polyether urethane samples which was not implanted, and FIG. 3 shows one of the polyether urethane samples which was implanted and following the one month explant. It will be readily seen when comparing FIGS. 2 and 3, that substantial breaking, cracking and degradation of the fibers of the polyether urethane sample has occurred in as little as one month during the in vivo implant.

Figure 4:
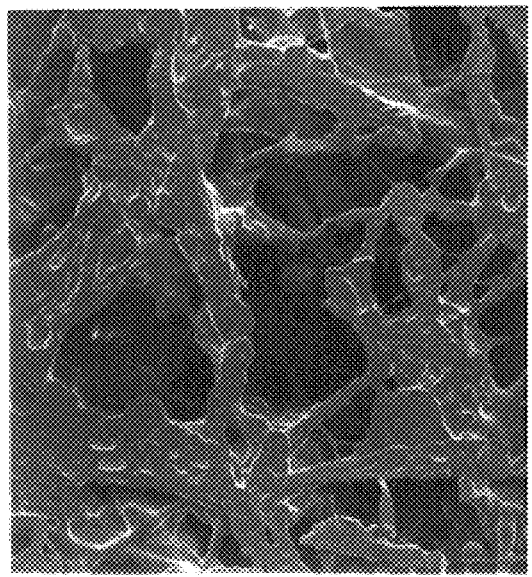
FIGS. 4 and 5 are photomicrographs of sections of triblock polymer material samples which respectively have not and have been in vivo implanted and of the kind which is the subject of the present invention for in vivo implant use.
Figure 5:
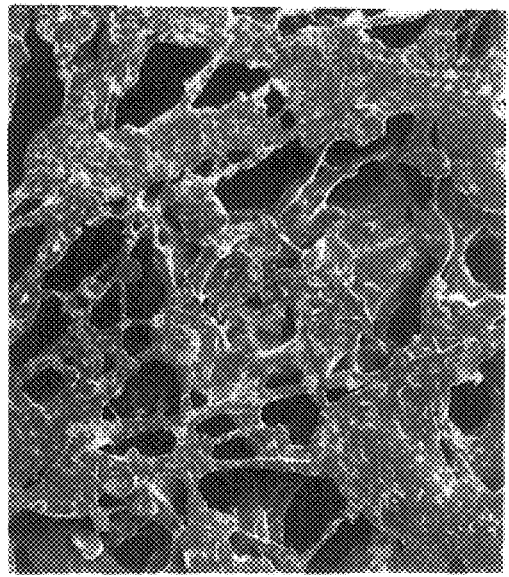

FIGS. 4 and 5 are reproductions of photomicrographs of the samples of the triblock polymer of the invention also at 200× under the electron microscope. Although FIGS. 2 and 3 and 4 and 5, respectively, do appear to be somewhat structurally different from each other in the drawing, this difference is not the result of the presence or absence of degradation of the polymer. It is simply the difference in the fiber diameters of the respective membranes and also the difference in structure between the respective membranes and how they were formed on the rotating mandrel, i.e. the polyether urethane of FIGS. 2 and 3 having been first formed into fibers which are wound upon the rotating mandrel, and the triblock polymer of the invention and of FIGS. 4 and 5 having simply been sprayed with an air brush directly on the mandrel.

FIG. 4 shows one of the triblock polymer samples of the invention which was not implanted, and FIG. 5 shows one of the triblock polymer samples of the invention which was implanted and following the three month explant. It will be seen when comparing FIGS. 4 and 5 that the explanted sample appears very similar to the non-implanted control sample, and no substantial breaking, cracking or degradation of the triblock polymer sample of the invention occurred in the three months during the in vivo implant, and in contrast to the explanted polyether urethane sample shown in FIG. 3.

It will be understood that the embodiments of the present invention which have been described are illustrative of some of the applications of the principles of the present invention. Various modifications may be made by those skilled in the art without departing from the true spirit and scope of the invention.

I claim:

1. A method of making an endoluminal or vascular device for in vivo implant and which is formed of a polymer which is resistant to degradation and cracking when in vivo implanted, comprising the steps of:
    applying the polymer when in fluid form on a surface;
    solidifying the polymer from its fluid form on the surface to form a non-woven membrane mat; and
    removing the non-woven membrane mat from the surface,
    wherein said polymer is a polyolefin copolymer;
    said polyolefin copolymer having a backbone in which the majority of polymer linkages along the copolymer chain are alternating quaternary and secondary carbon atoms;
    said polyolefin copolymer being a reaction product of a first rubbery component having a quaternary carbon atom which when homopolymerized produces a polymer having a low level of hardness, and a second hardening component which when homopolymerized produces a polymer having a high level of hardness; and
    said polyolefin copolymer reaction product of said first and second components is elastomeric and having a hardness intermediate said low and high levels of hardness.

2. The method of claim 1, wherein said surface is rotated as the polymer is sprayed thereon.

3. The method of claim 1, wherein the polymer is dissolved in a solvent, and is applied to said surface while in fluid form by spraying thereon, and the solvent is evaporated while spraying to form said non-woven membrane mat on the surface.

4. The method of claim 1, wherein the solidified polymer is an elastic copolymer.

5. The method of claim 1, wherein the non-woven membrane mat is porous.

6. The method of claim 1, wherein said polyolefin copolymer reaction product is a star or linear copolymer.

7. The method of claim 1, wherein said first rubbery component is polyisobutylene.

8. The method of claim 7, wherein said second hardening component is selected from the group consisting of styrene, α-methylstyrene, methylmethacrylate, ethylmethacrylate and hydroxyethyl methacrylate.

9. The method of claim 1, wherein said second hardening component is selected from the group consisting of styrene, α-methylstyrene, methylmethacrylate, ethylmethacrylate and hydroxyethyl methacrylate.

10. The method of claim 1, wherein said surface if rotated and the polymer is dissolved in a solvent and applied to said rotating surface while in fluid form by spraying thereon, and the solvent is evaporated while spraying to form said non-woven membrane mat on the surface; the solidified polymer is an elastic copolymer; and the non-woven membrane mat is porous.

11. The method of claim 1, wherein said polymer is applied to said surface by spraying.

12. A method of making an endoluminal or vascular device for in vivo implant and which is formed of a polymer which is resistant to degradation and cracking when in vivo implanted, comprising the steps of:
    applying the polymer when in fluid form on a surface;
    solidifying the polymer from its fluid form on the surface to form a non-woven membrane mat; and
    removing the non-woven membrane mat from the surface,
    wherein the reaction product has the formulation:

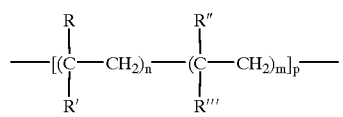

where R and R' are non-cyclic or cyclic aliphatic moieties having from 1 to about 8 carbon atoms, R" is a hydrogen, hydroxyl, methyl or ethyl group, and R''' is an aromatic phenyl, benzyl or substituted benzyl group, COOCH$_3$, methoxy, ethoxy, aliphatic, cycloaliphatic, or substituted aliphatic, and such that homopolymers of

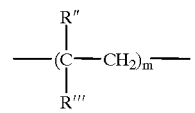

have a high level of hardness, n and m are from about 250 to about 5000, and p is about 1–10.

13. A method of making an endoluminal or vascular device for in vivo implant and which is formed of a polymer which is resistant to degradation and cracking when in vivo implanted, comprising the steps of:
    applying the polymer when in fluid form on a surface;
    solidifying the polymer from its fluid form on the surface to form a non-woven membrane mat; and
    removing the non-woven membrane mat from the surface,
    wherein the reaction product has the formulation:

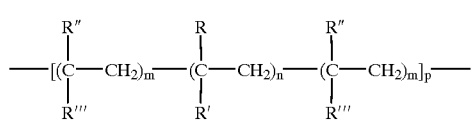

where R and R' are non-cyclic or cyclic aliphatic moieties having from 1 to about 8 carbon atoms, R" is a hydrogen, hydroxyl, methyl or ethyl group, and R''' is an aromatic phenyl, benzyl or substituted benzyl group, COOCH₃, methoxy, ethoxy, aliphatic, cycloaliphatic, or substituted aliphatic, and such that homopolymers of

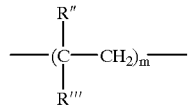

have a high level of hardness, n and m are from about 250 to about 5000, and p is about 1–10.

14. A method of making an endoluminal or vascular device for in vivo implant and which is formed of a polymer which is resistant to degradation and cracking when in vivo implanted, comprising the steps of:
applying the polymer when in fluid form on a surface;
solidifying the polymer from its fluid form on the surface to form a non-woven membrane mat; and
removing the non-woven membrane mat from the surface,
wherein said surface is rotated as the polymer is sprayed thereon; the polymer which is sprayed while in fluid form is dissolved in a solvent, and the solvent is evaporated while spraying to form said non-woven membrane mat on the surface; the solidified polymer is an elastic copolymer; and the non-woven membrane mat is porous,
wherein said polymer is a polyolefin copolymer;
said polyolefin copolymer having a backbone in which the majority of polymer linkages along the copolymer chain are alternating quaternary and secondary carbon atoms;
said polyolefin copolymer being a reaction product of a first rubbery component having a quaternary carbon atom which when homopolymerized produces a polymer having a low level of hardness, and a second hardening component which when homopolymerized produces a polymer having a high level of hardness; and
said polyolefin copolymer reaction product of said first and second components is elastomeric and having a hardness intermediate said low and high levels of hardness.

15. The method of claim 14, wherein said polyolefin copolymer reaction product is a star or linear copolymer.

16. The method of claim 14, wherein said first rubbery component is polyisobutylene.

17. The method of claim 16, wherein said second hardening component is selected from the group consisting of styrene, α-methylstyrene, methylmethacrylate, ethylmethacrylate and hydroxyethyl methacrylate.

18. The method of claim 14, wherein said second hardening component is selected from the group consisting of styrene, α-methylstyrene, methylmethacrylate, ethylmethacrylate and hydroxyethyl methacrylate.

19. A method of making an endoluminal or vascular device for in vivo implant and which is formed of a polymer which is resistant to degradation and cracking when in vivo implanted, comprising the steps of:
applying the polymer when in fluid form on a surface;
solidifying the polymer from its fluid form on the surface to form a non-woven membrane mat; and
removing the non-woven membrane mat from the surface,
wherein said surface is rotated as the polymer is sprayed thereon; the polymer which is sprayed while in fluid form is dissolved in a solvent, and the solvent is evaporated while spraying to form said non-woven membrane mat on the surface; the solidified polymer is an elastic copolymer; and the non-woven membrane mat is porous,
wherein the reaction product has the formulation:

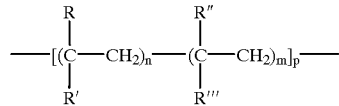

where R and R' are non-cyclic or cyclic aliphatic moieties having from 1 to about 8 carbon atoms, R'' is a hydrogen, hydroxyl, methyl or ethyl group, and R''' is an aromatic phenyl, benzyl or substituted benzyl group, COOCH₃, methoxy, ethoxy, aliphatic, cycloaliphatic, or substituted aliphatic, and such that homopolymers of

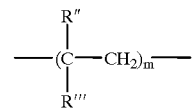

have a high level of hardness, n and m are from about 250 to about 5000, and p is about 1–10.

20. A method of making an endoluminal or vascular device for in vivo implant and which is formed of a polymer which is resistant to degradation and cracking when in vivo implanted, comprising the steps of:
applying the polymer when in fluid form on a surface;
solidifying the polymer from its fluid form on the surface to form a non-woven membrane mat; and
removing the non-woven membrane mat from the surface,
wherein said surface is rotated as the polymer is sprayed thereon; the polymer which is sprayed while in fluid form is dissolved in a solvent, and the solvent is evaporated while spraying to form said non-woven membrane mat on the surface; the solidified polymer is an elastic copolymer; and the non-woven membrane mat is porous,
wherein the reaction product has the formulation:

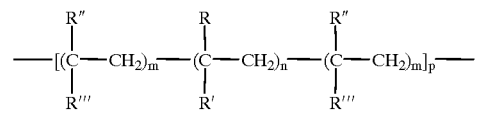

where R and R' are non-cyclic or cyclic aliphatic moieties having from 1 to about 8 carbon atoms, R'' is a hydrogen, hydroxyl, methyl or ethyl group, and R''' is an aromatic phenyl, benzyl or substituted benzyl group, COOCH₃, methoxy, ethoxy, aliphatic, cycloaliphatic, or substituted aliphatic, and such that homopolymers of

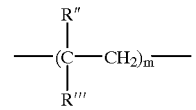

have a high level of hardness, n and m are from about 250 to about 5000, and p is about 1–10.

* * * * *